(12) United States Patent    (10) Patent No.: US 8,668,400 B2
Ecker et al.    (45) Date of Patent: Mar. 11, 2014

(54) FLUID APPLICATOR

(75) Inventors: William Ecker, Stamford, CT (US); George Engel, Edison, NJ (US); Bruce Harvie, Piscataway, NJ (US); Vitor Oliveira, Elizabeth, NJ (US)

(73) Assignee: The Hartz Mountain Corporation, Secaucus, NJ (US)

( * ) Notice: Subject to any disclaimer, the term of this patent is extended or adjusted under 35 U.S.C. 154(b) by 1171 days.

(21) Appl. No.: 12/058,562

(22) Filed: Mar. 28, 2008

(65) Prior Publication Data

US 2008/0245380 A1    Oct. 9, 2008

Related U.S. Application Data

(60) Provisional application No. 60/910,410, filed on Apr. 5, 2007.

(51) Int. Cl.
B43K 5/14    (2006.01)
(52) U.S. Cl.
USPC ............................... 401/134; 119/603; 222/91
(58) Field of Classification Search
USPC ..................... 401/134; 604/3; 222/91, 89, 83; 119/602–605, 650–652, 656, 658, 659; 239/288; 16/226; 362/35
See application file for complete search history.

(56) References Cited

U.S. PATENT DOCUMENTS 1,219,641 A * 3/1917 Humphrey .................... 239/288
2,197,579 A   4/1940 Hooper
3,378,168 A   4/1968 Hildebrandt
3,402,855 A   9/1968 Schroeder et al.
3,477,447 A   11/1969 Elredge
3,744,678 A * 7/1973 Beres et al. .................... 222/205
3,940,003 A   2/1976 Larson
RE29,656 E   6/1978 Chittenden et al.

(Continued)

FOREIGN PATENT DOCUMENTS

EP    93090    11/1983
EP    1584573    10/2005

(Continued)

OTHER PUBLICATIONS

Office Action, dated Feb. 2, 2011, in Canadian Patent Appln. No. 2,682,678, filed on Apr. 2, 2008.

(Continued)

*Primary Examiner* — Len Tran
*Assistant Examiner* — Viet Le
(74) *Attorney, Agent, or Firm* — Stroock & Stroock & Lavan LLP

(57) ABSTRACT

An applicator tip is provided for operating in conjunction with a pierceable fluid reservoir. Assemblies in accordance with the invention can lead to an exceptionally easy to use, safe, and convenient system and method of applying a fixed dosage of chemicals to which a user might wish to avoid contact, such as parasiticides. The cap-applicator can have an internal piercing tip capable of piercing the reservoir when the assembly is converted into an active configuration. Projections can be provided, in the form of fins on a tube or a multi-prong structure with straight or curved projections. The tips of one or more projections can include dispensing ports or the ports can be recessed from the distal tip, such as in a notch, so as not to be obstructed if the distal tip of the cap is pressed against an animal to dispense the fluid.

13 Claims, 14 Drawing Sheets

(56) References Cited

U.S. PATENT DOCUMENTS

| | | | |
|---|---|---|---|
| 4,307,821 A | | 12/1981 | McIntosh |
| 4,482,069 A | | 11/1984 | Stadler |
| 4,585,018 A | | 4/1986 | O'Connor |
| 4,854,760 A | * | 8/1989 | Pike et al. .................... 401/134 |
| 5,042,690 A | | 8/1991 | O'Meara |
| 5,052,589 A | | 10/1991 | O'Meara |
| 5,163,583 A | | 11/1992 | Whitworth |
| 5,427,275 A | | 6/1995 | Hansen |
| 5,632,315 A | * | 5/1997 | Rose ........................... 141/329 |
| 5,711,453 A | | 1/1998 | Weiler |
| 5,772,652 A | | 6/1998 | Zielinski |
| 5,879,345 A | | 3/1999 | Aneas |
| 5,925,029 A | | 7/1999 | Jansen et al. |
| 5,954,233 A | | 9/1999 | Kawashima et al. |
| 6,193,108 B1 | | 2/2001 | Lepsius et al. |
| 6,238,372 B1 | | 5/2001 | Zinger et al. |
| 6,292,431 B1 | | 9/2001 | Seymour et al. |
| 6,293,431 B1 | | 9/2001 | Seymour et al. |
| 6,302,607 B1 | | 10/2001 | Burrowes |
| 6,379,340 B1 | | 4/2002 | Zinger et al. |
| 6,464,105 B1 | | 10/2002 | Rolle et al. |
| 6,601,721 B2 | | 8/2003 | Jansen et al. |
| 6,626,309 B1 | | 9/2003 | Jansen et al. |
| 6,726,060 B1 | | 4/2004 | Ragusa et al. |
| 6,886,716 B2 | | 5/2005 | Weiler |
| 6,932,532 B2 | | 8/2005 | Schwartzman et al. |
| 6,971,548 B2 | | 12/2005 | Smith |
| 7,114,635 B2 | | 10/2006 | Yamada |
| 7,207,465 B2 | * | 4/2007 | Weist ............................... 222/83 |
| 2003/0006247 A1 | | 1/2003 | Olivier |
| 2004/0200855 A1 | | 10/2004 | Weiler |
| 2005/0029288 A1 | | 2/2005 | Heldt et al. |
| 2005/0269353 A1 | | 12/2005 | Cabelli |
| 2005/0269354 A1 | | 12/2005 | Smtih |
| 2005/0279761 A1 | * | 12/2005 | Weiler et al. .................... 222/83 |
| 2006/0011666 A1 | | 1/2006 | Wurtz et al. |
| 2006/0131327 A9 | | 6/2006 | Cabelli |
| 2006/0184103 A1 | | 8/2006 | Paproski et al. |

FOREIGN PATENT DOCUMENTS

| | | |
|---|---|---|
| GB | 512681 | 9/1939 |
| GB | 512681 A | 9/1939 |
| JP | 09-323741 | 12/1997 |
| JP | 10-92364 | 7/1998 |
| JP | 10-230960 A | 9/1998 |
| JP | 2002-002761 A | 1/2002 |
| JP | 2004-049339 A | 2/2004 |
| WO | WO 94/20379 | 9/1994 |
| WO | WO 94/20379 A1 | 9/1994 |
| WO | WO 2007/022653 | 3/2007 |
| WO | WO 2007/022653 A1 | 3/2007 |

OTHER PUBLICATIONS

International Search Report and Written Opinion from the International Searching Authority (US) for International Application No. PCT/US2008/059054 dated Aug. 6, 2008.

International Search Report and Written Opinion from the International Searching Authority (US) for International Application No. PCT/US2008/059168 dated Aug. 8, 2008.

Extended Search Report, dated Aug. 31, 2011, in European Patent Appln. No. 08733078.3, filed on Apr. 2, 2008.

Extended Search Report, dated Aug. 31, 2011, in European Patent Appln. No. 08754898.8, filed on Apr. 1, 2008.

First Office Action issued on Sep. 1, 2011 in corresponding Chinese Patent Appln. No. 200880018099.0.

First Office Action issued on Sep. 22, 2011 in corresponding Chinese Patent Appln. No. 200880011464.5.

Extended Search Report issued on Sep. 19, 2011 in the corresponding European Patent Appln. No. 08754898.8.

Office action issued on Jan. 11, 2012 in Canadian Application 2,682,901.

Office Action issued on Mar. 4, 2013 in corresponding Japanese Patent Appln. No. 2010-502248, filed on Apr. 1, 2008, with English translation of Notification of Reason for Rejection.

* cited by examiner

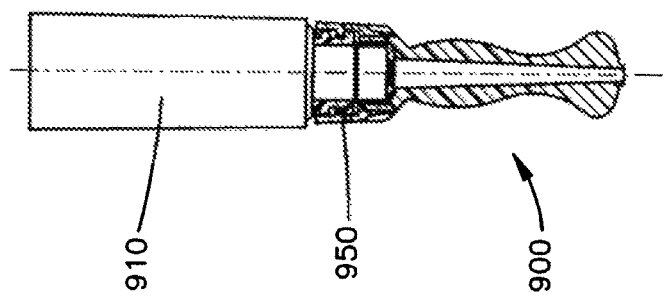
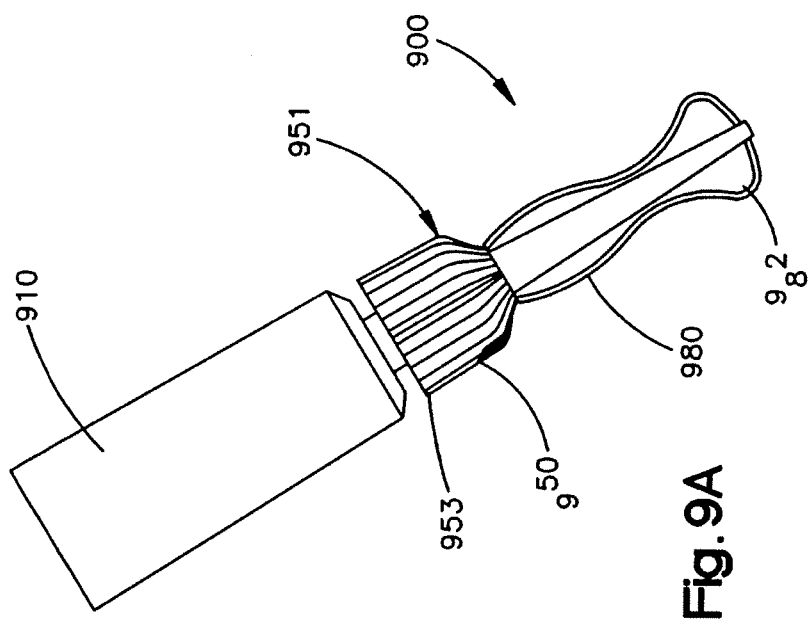

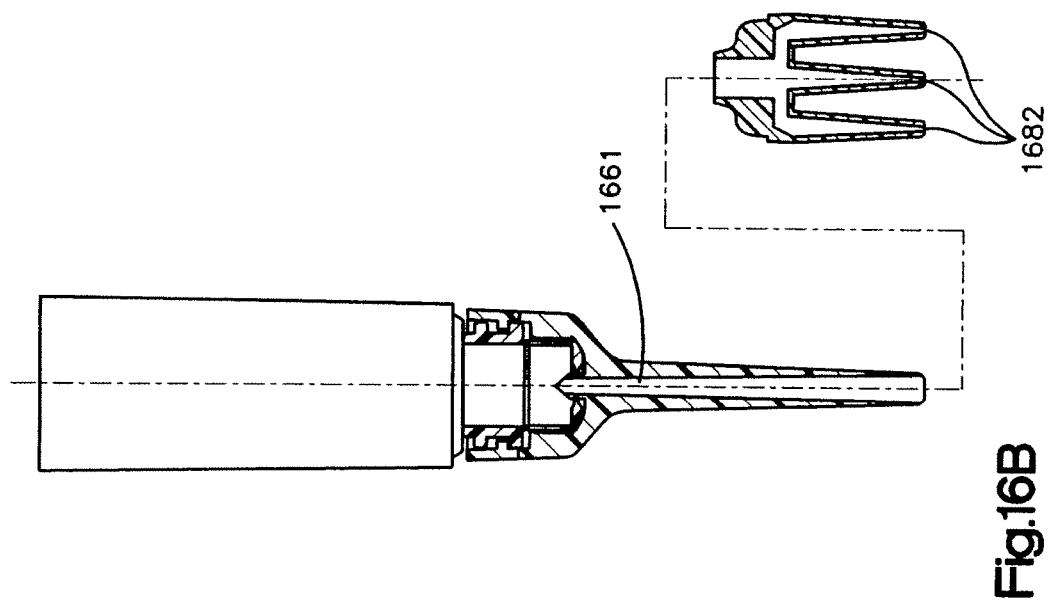
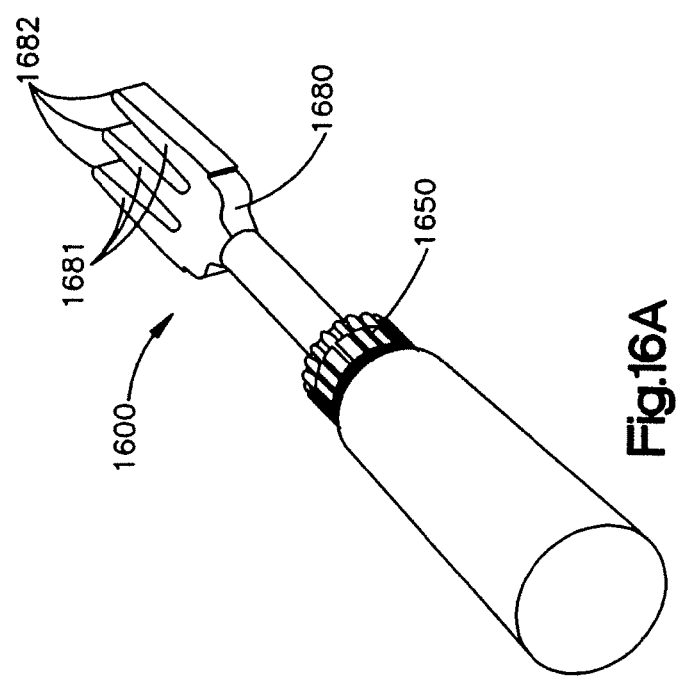

FLUID APPLICATOR

This non-provisional utility patent application claims priority to and the benefit of U.S. provisional application No. 60/910,410, filed Apr. 5, 2007, the contents of which is incorporated herein by reference.

BACKGROUND OF THE INVENTION

This invention relates to a fluid or gel delivery assembly, and more particularly to a system for delivering fluid or gel from a sealed container. As used herein, references to fluids should be understood to also refer to gels and gel like substances and liquids, whether or not they are technically fluids.

Applicators for delivering quantities of fluid are well known in the art. Numerous variations exist to account for different purposes. However, there is an unsolved need for a cost-effective, easy to use, and safe mechanism for delivering product with minimal exposure to the dispenser while allowing for maximum dispensing of the total reservoir volume, for example, a topical parasiticide to the coat and skin of an animal.

Biologically or chemically active fluid often requires a sealed container for storage. A bottle with a cap and an opening may allow some leakage, bacterial contamination or evaporation of the active fluid or permit some ambient air to enter the bottle. Thus, it is desirable to enclose such active ingredient in a sealed environment.

Furthermore, a typical reservoir of parasiticide or other fluid or gel may require the attachment of a separate applicator. When attaching an applicator to the reservoir of many known containers, the user must engage the applicator with the reservoir after opening the reservoir, either by uncapping the reservoir or piercing the reservoir. The opening of the reservoir and the subsequent manipulation of attaching the applicator forces pet owners to come into contact with the parasiticide, glue or other chemical or at least cause concerns about leakage, mess, or the application of maximum prescribed dose.

Additional concern arises when consumers store sensitive chemicals in opened containers. The chemical may lose effectiveness over time, evaporate or even transforms into harmful substance. Thus, it is desirable to provide a liquid delivery assembly that discourages user from retaining such chemicals in an opened container.

Another challenge for providers of sensitive chemicals such as a parasiticide is dosage. It may be difficult for some users to measure the right amount to dispense. Thus, it is desirable to provide a liquid delivery assembly that delivers a pre-determined amount of active chemicals corresponding to the size and weigh of the patient.

Another challenge for users of animal parasiticides is the ability to distribute the parasiticide through out the affected area of the animal. Thus, it is an advantage of the invention to provide a liquid delivery assembly capable of easily reaching beneath the fur and distributing the anti-parasite material, such as parasiticides, onto the skin.

Accordingly, it is desirable to provide an improved fluid or gel delivery system that overcomes drawbacks of existing systems.

SUMMARY OF THE INVENTION

Generally speaking, in accordance with the invention, an applicator tip is provided for operating in conjunction with a pierceable fluid reservoir. Assemblies in accordance with the invention can lead to an exceptionally easy to use, safe, and convenient system and method of applying a fixed dosage of chemicals to which a user might wish to avoid contact, such as parasiticides. In the present invention, a fluid, such as a pesticide or parasiticide, glue, solvent, lubricant, medicament and the like is loaded into a fluid reservoir and the reservoir sealed. The reservoir can be attached to a cap-applicator structure which is in an inactive configuration. In the inactive configuration, a piercing tip remains poised over the reservoir in an inactive configuration without forming an opening in the reservoir. The cap-applicator can have a sharp internal piercing tip capable of piercing the reservoir when the assembly is converted into an active configuration. This will allow the user to dispense the liquid out of the reservoir through the applicator. The force needed to dispose the cap from the poised inactive condition to the active pierced condition can be a matter of design choice to prevent unintentional piercing and preferably involve providing positive feedback in the form of a jolt or click to let a user know the reservoir has been pierced. Assemblies in accordance with preferred embodiments of the invention can provide easy to use devices for delivery of fluids or gels that minimizes undesirable contact, spill, waste or mess. A stable engagement between the cap and the reservoir advantageously ensures that no leakage will occur between the interface of the cap and the reservoir during activation and use. Structures are also desirable for keeping the applicator assembly in the active configuration. Projections can be provided, in the form of fins on a tube or a multi-prong structure with straight or curved projections. The tips of one or more projections can include dispensing ports or the ports can be recessed from the distal tip, such as in a notch, so as not to be obstructed if the distal tip of the cap is pressed against an animal to dispense the fluid.

In another embodiment of the invention, the tip of the cap-applicator is in the shape of a comb (with multiple projections, which can be in a forked or rake-like configuration, one or more of which can have fluid delivery ports) or finned spreader, designed to part an animal's fur and more evenly spread the insecticide on the animal.

Thus, it is an advantage of the invention to provide a sealed, shelf-stable environment whereby the fluid may remain stable.

It is a further advantage of the invention to provide a cap with an applicator tip and the liquid reservoir already assembled and obviate any manipulation to attach a separate cap or applicator to an opened reservoir, which in turn remove the danger that and user may accidentally come into undesirable contacts with the liquid or gel.

It is an additional advantage of the invention to provide a pierceable liquid reservoir system that discourages the user from storing an open container and potentially unstable parasiticide for future use.

It is an additional advantage of the invention to provide a mechanism for dispensing a predetermined amount of parasiticide to a specific location at a precise dose in line with the recommended volume required for treatment.

Other objects and features of the present invention will become apparent from the following detailed description, considered in conjunction with the accompanying drawing figures. It is to be understood, however, that the drawings are designed solely for the purpose of illustration and not as a definition of the limits of the invention.

BRIEF DESCRIPTION OF THE FIGURES

For a fuller understanding of the invention, reference is had to the following description, taken in connection with the accompanying drawings, in which:

FIGS. 9A, 9B and 9C are side plan, perspective and cut-away views, respectively, of the fluid delivery assembly for accordance with an embodiment of the invention.

FIGS. 16A and 16B are perspective and cut-away views of a cap of a fluid delivery assembly in accordance with another embodiment of the invention.

DETAILED DESCRIPTION OF THE PREFERRED EMBODIMENT

Figure 1A:
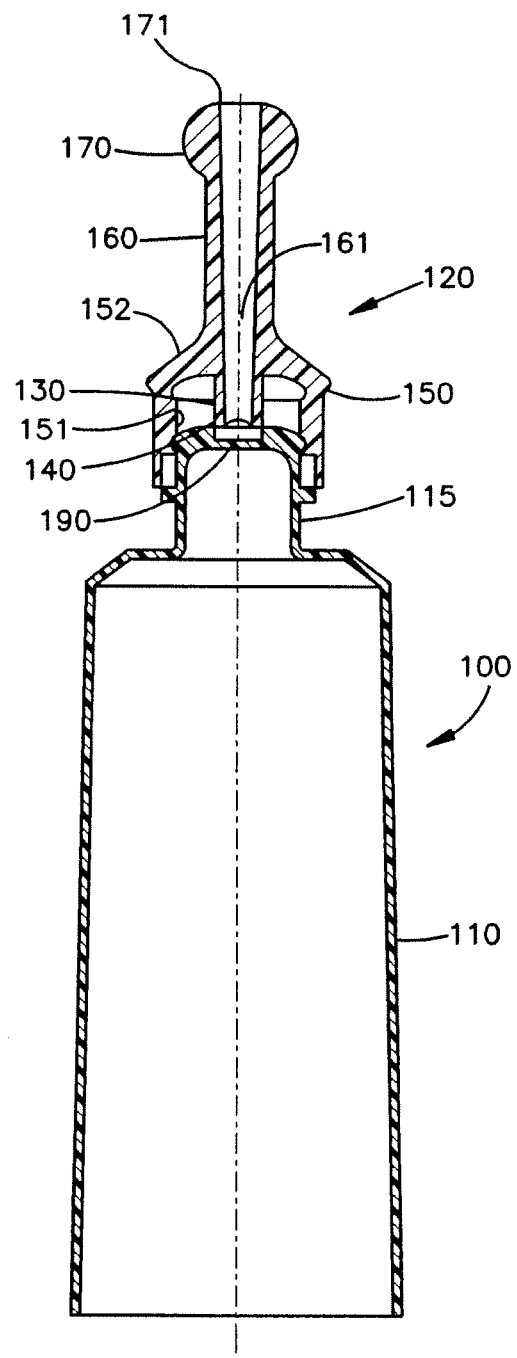
FIGS. 1A and 1B are partial cross-sectional views of a fluid delivery assembly in accordance with an embodiment of the invention in the pre-activation and post-activation conditions, respectively.

The components of the liquid delivery assembly in accordance with preferred embodiments of the invention can be manufactured via known methods of plastic molding and manufacture, the details of which will be apparent to those having skill in the art. The precise shapes and sizes of the components described herein are not necessarily essential to the invention, since the invention is described with reference to illustrative embodiments.

A preferred fluid delivery assembly in accordance with the invention comprises a dispensing cap having an applicator extension or tube, an interior piercing tip, a hollow channel extending throughout said piercing tip to the applicator tube and a base attachable to an external fluid reservoir. A sealed fluid reservoir having a region pierceable by said piercing tip on the cap is engaged to the cap. A multi-stage detent mechanism on said dispensing cap and fluid reservoir will allow said dispensing cap to captively engage said fluid reservoir in at least one inactive configuration where the fluid reservoir is not pierced and at least one active configuration where the fluid reservoir is pierced. Such multi-stage detent mechanism is also capable of preventing said piercing tip from piercing said reservoir until a user elects to convert said inactive configuration into said active configuration.

Fluid reservoirs in accordance with the invention should be substantively inactive to the fluid or gel stored therein, pliable enough to allow fluid to be squeezed out, but hard enough to engage the cap portion to keep the cap from detaching or prematurely shifting into the active configuration. A non-exhaustive list of acceptable materials for the reservoir includes propylene, etaylene, nylon, k-resin, polypropylene, and polyethylene in either homo or copolymer versions.

Dispensing caps in accordance with the invention should be substantively inactive to the fluid or gel therein and sufficiently rigid to allow the piercing tip to puncture the fluid reservoir. A non-exhaustive list of acceptable materials for the cap includes propylene, etaylene, nylon, k-resin, polypropylene, polyethylene, polyoxymethylene, polyacetal, and aliphatic polyketones (Carilon).

A non-limiting example of a fluid delivery assembly constructed in accordance with preferred embodiments of the invention is shown generally as fluid delivery system 100 in FIG. 1. It will be appreciated that fluid delivery systems identified herein can also be used to deliver gels, with little or no modification. Delivery system 100 includes a hollow fluid reservoir 110 or another suitable fluid delivering tube or source engaged with a dispensing cap 120. Reservoir 110 stores the fluid or gel therein. In a preferred embodiment of the invention, reservoir 110 stores a single dose of pesticide for a dog, cat, horse or other animal of appropriate size.

Dispensing cap 120 includes a short hollow cylindrical tube 130, which terminates in a slanted piercing tip 140. Tube 130 can be of uniform width and extends perpendicularly from within an interior 151 of a dome 150 of dispensing cap 120. Tube 130 serves as a conduit from reservoir 110 to cap 120. Cap 120 is designed to selectively form an opening in reservoir 110 and provide a tip to dispense the fluid or gel therein in a convenient manner.

Cap 120 also includes an extended applicator tube 160, which can be unitary with and extend from the top of dome 150. Applicator tube 160 terminates in a nozzle 170. Tube 160 defines a channel 161, which extends from piercing tip 140, through short tube 130 to nozzle 170 and defines a liquid passageway capable of communicating fluid from piercing tip 140 to a nozzle end 171.

It should be appreciated that extended applicator tube 160 and applicator nozzle 170 may adopt a variety of shapes and sizes consistent with different usage, other than what is depicted in FIG. 1. For example, the extended applicator tube may be longer or shorter and may contain a bend, a flare or a constriction. Applicator nozzle 170 may taper into a narrow tip or contain one or more fur-spreading fin structures for accessing difficult to reach areas or terminate in a rounded blunt bulge to avoid damaging the skin of the pet when applying a parasiticide. In one embodiment of the invention, extended tube 160, channel 161 and nozzle 170 can be conical, so that trimming back the tip can increase the diameter of the opening at the tip of channel 161. The present invention is not limited to the extended applicator tube and applicator nozzle presented herein.

It should be appreciated that the external surface of dome 150 may adopt a variety of features to facilitate usage. For example, an external surface top face 152 of dome 150 may contain a plurality of ridges capable of providing the user a firm grip during activation.

Figure 1B:
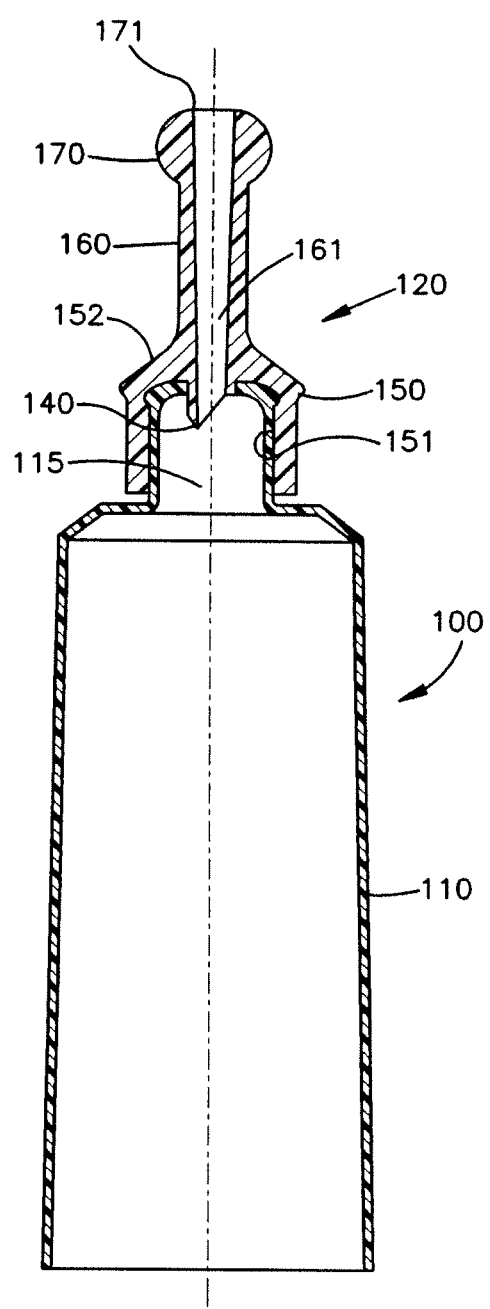

Fluid reservoir 110 includes a reservoir tip 115. An upper end of tip 115 includes a pierceable region 190, whereby the surface of the pierceable region 190 is proximal and perpendicular to cylindrical tube 130 when fluid reservoir 110 and dispensing cap 120 are engaged in an inactive position as shown in FIG. 1A. Pierceable region 190 should be sufficiently wide to receive the outside diameter of cylindrical tube 130 when fluid reservoir 110 and dispensing cap 120 are engaged in an active configuration as shown in FIG. 1B. The area of pierceable region 190 may be adjusted to balance the force required for piercing against the force feedback once piercing occurs. To further reduce the force of piercing, the thickness of the material in the pierceable region 190 may be adjusted so that the outer diameter of pierceable region 190 is thinner than at its center.

Generally, the fluid reservoir and the dispensing cap should be appropriately sized with respect to the space within the dome of the dispensing cap, allowing the fluid reservoir and the dispensing cap to move from the inactive configuration to active configuration.

Fluid delivery assemblies in accordance with the invention can contain a multi-stage detent mechanism to provide multi-stage engagement, while preventing unintended activation due to inadvertent piercing of the fluid reservoir.

Figure 2:
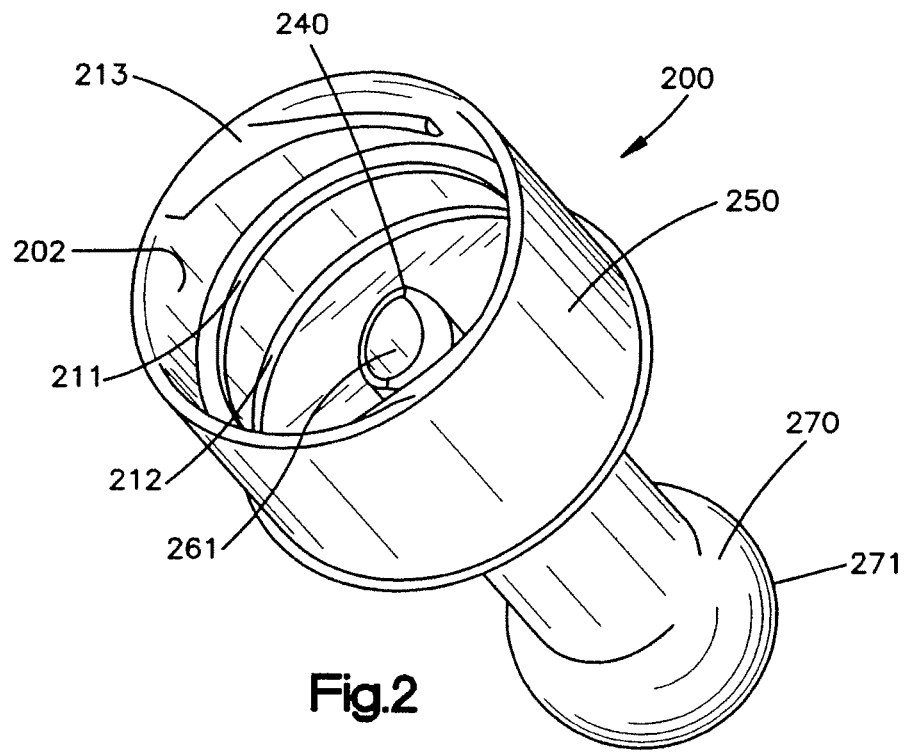
FIG. 2 is a perspective view of a dispensing cap component for a fluid delivery assembly in accordance with an a embodiment of the invention.

A dispensing cap 200 in accordance with another embodiment of the invention is shown generally in FIG. 2. Cap 200 is configured to work with a reservoir tip 300 shown generally in FIG. 3. A multi-stage detent between cap 200 and tip 300 is provided as a ridge 310 on an external surface 301 of fluid reservoir tip 300 and two retaining grooves 211 and 212 on an internal wall surface 202 of dispensing cap 200.

In an inactive configuration, ridge 310 engages retaining groove 211 and dispensing cap 200 is captively held on tip 300 of a fluid reservoir 350 during transport or storage without piercing a pierceable region 390 of fluid reservoir tip 300.

In an active configuration, ridge 310 engages retaining groove 212 and dispensing cap 200 is captively held on tip 300 of fluid reservoir 350 while a piercing tip 240 penetrates piercing region 390. This brings the fluid content in an interior 351 of reservoir 350 into communication with a channel 261 of dispensing cap 200, allowing the contents of fluid reservoir 350 to enter and flow through hollow channel 261 from piercing tip 240 and exit through a tip 271 of an applicator nozzle 270.

Internal wall 202 of dome 205 of dispensing cap 200 is provided with screw threads 213 about internal wall 202 thereof. Screw threads 213 are threadingly engageable with corresponding screw threads 314 on fluid reservoir 300. The threading engagement between screw threads 213 and 314 ensures that piercing tip 240 will not breach fluid reservoir 300 at pierceable region 390 unless the user deliberately converts the inactive configuration into the active configuration by turning dispensing cap 200 in relation to fluid reservoir 300 to urge cap 200 and piercing tip 240 towards reservoir 300 and pierceable region 390 until ridge 310 of fluid reservoir 300 engages retaining groove 212 of dispensing cap 200. Thus, after cap 200 is urged out of its retained state in the inactive position, it becomes retained in the active state.

Figure 3:
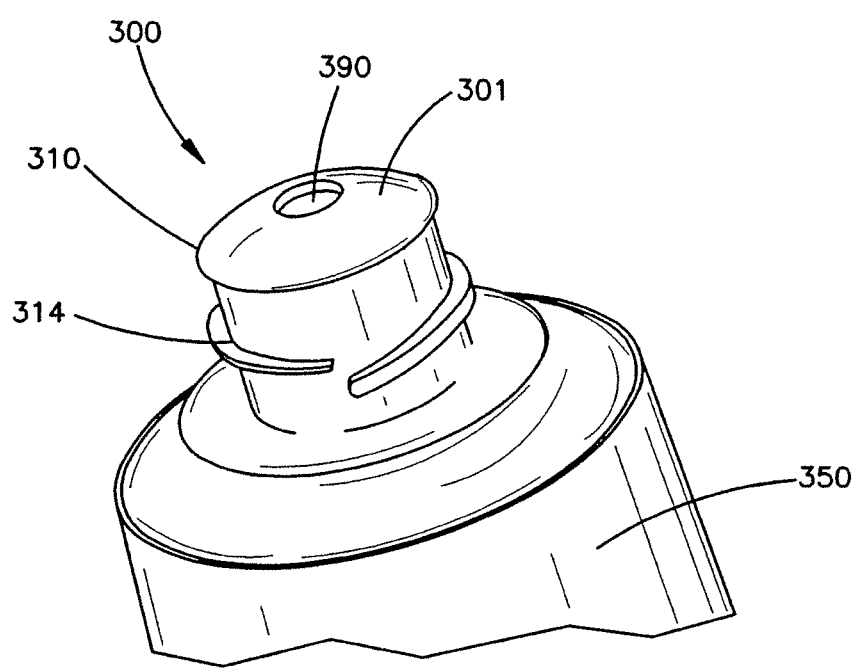
FIG. 3 is a partial perspective view of a fluid reservoir component of a fluid delivery assembly in accordance with an a embodiment of the invention.

It should be appreciated that other type of detent mechanism may be used instead of the mechanism shown in FIG. 2 and FIG. 3. For example, the ridge may be present on the interior surface of the dispensing cap and two matching retaining grooves may be present on the fluid reservoir. Other multi-stage detent mechanisms are suitable as well. The present invention is not limited to the selection of the engaging mechanisms presented herein.

Figure 4A:
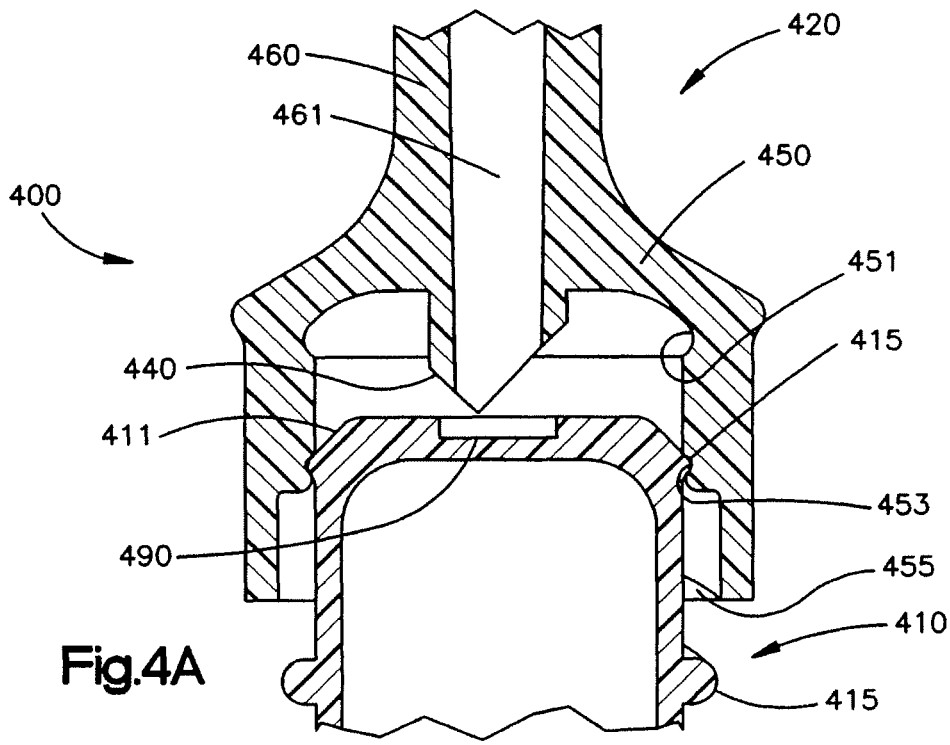
FIGS. 4A and 4B are cross-sectional views of a fluid delivery assembly in accordance with an embodiment of the invention in the pre-activation and post-activation conditions, respectively.
Figure 4B:
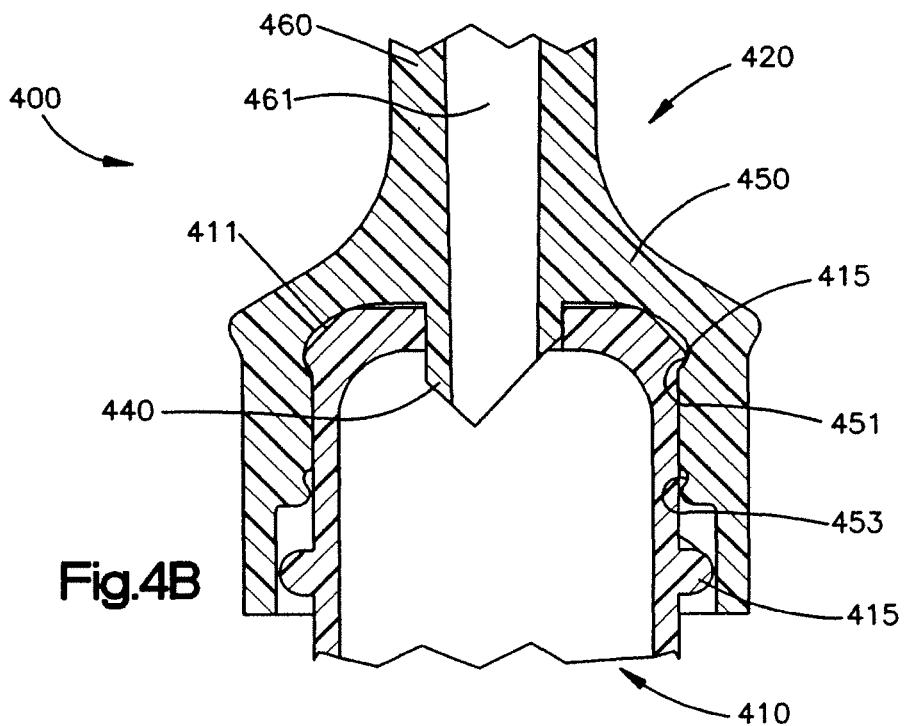

The features of another preferred embodiment of the invention are shown in FIGS. 4A and 4B as assembly 400. A dispensing cap 420 is configured to work with a reservoir tip 410. Multi-stage detention between cap 420 and tip 410 is accomplished via use of a ridge 415 on an external surface 411 of fluid reservoir tip 410 and two retaining grooves 451 and 453 inside and unitary with a base 450 of dispensing cap 420.

In an inactive configuration, ridge 415 engages retaining groove 453 and dispensing cap 420 is captively held on tip 410 of a fluid reservoir during transport or storage without piercing a pierceable region 490 of fluid reservoir tip 410.

In an active configuration, ridge 415 engages retaining groove 451 and dispensing cap 420 is captively held on tip 410 of a fluid reservoir 401 while a piercing tip 440 penetrates a piercing region 490 on tip 410. This brings the fluid content in interior of reservoir 401 into communication with a channel 461 of dispensing cap 420, allowing the contents of fluid reservoir 401 to enter hollow channel 461 from piercing tip 440 and exit through cap 420.

To prevent accidental activation, screw threading 455 inside base 450 of cap 420 is threadingly engageable with corresponding screw threading 415 on tip 410. The threading mechanism ensures that piercing tip 440 will not breach pierceable region 490 unless the user deliberately converts the inactive configuration into the active configuration by turning dispensing cap 420 in relation to tip 410 until ridge 415 engages retaining groove 451 of dispensing cap 420.

In accordance with a preferred embodiment of the invention, piercing tip 440 is designed with a slant (which can be symmetrical or asymmetrical) to avoid a potential problem that a flap of material left on a piercing region 490 may partially cover the opening of a hollow channel 461 at piercing tip 440 and impede fluid flow. The angle for piercing tip 440 is preferably from 55° to 120° and most preferably from 60° to 90°.

Figure 5:
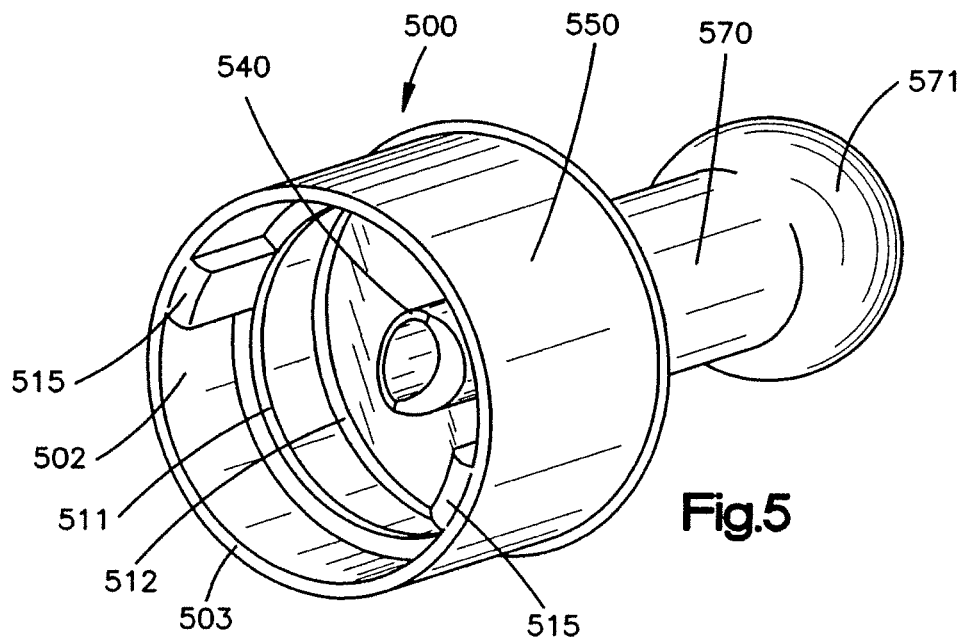
FIG. 5 is a perspective view of a dispensing cap component of a fluid delivery assembly in accordance with an embodiment of the invention.
Figure 6:
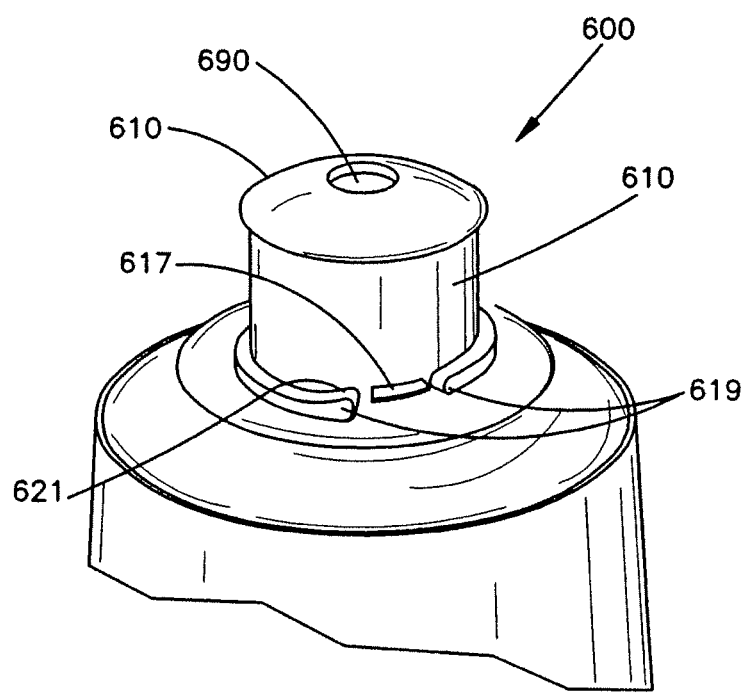
FIG. 6 is partial perspective view of a fluid reservoir component of a fluid delivery assembly in accordance with an embodiment of the invention.

In another preferred embodiment of the invention shown in FIG. 5 and FIG. 6, two regions of an internal wall 502 of a dome 550 of a dispensing cap 500 are raised to form a pair of tab breakers 515 that extends from an edge 503 of dome 550 to a first retaining groove 511. A pair of breakaway tabs 617 extends from an external surface 610 of a fluid reservoir 600. A pair of pre-activation rims 619 on fluid reservoir 600 extends from and are unitary with fluid reservoir 600. The pre-activation rims 619 are generally on the same plane with and flank breakaway tabs 617 without being directly connected with breakaway tabs 617. A pair of bump stops 621 are provided on one end of each pre-activation rims 619. The breakaway tab mechanism ensures that piercing tip 540 will not breach pierceable region 690 unless the user deliberately rotates dispensing cap 500 with enough deliberate force until the side of tab breakers 515 rests against bump stops 621 (at which point tab breakers 515 are poised over and aligned with breakaway tabs 617), and push dispensing cap 500 onto fluid reservoir 600, breaking breakaway tabs 517 from fluid reservoir 600, and form the retained activated configuration.

Figures 7A, 7B:
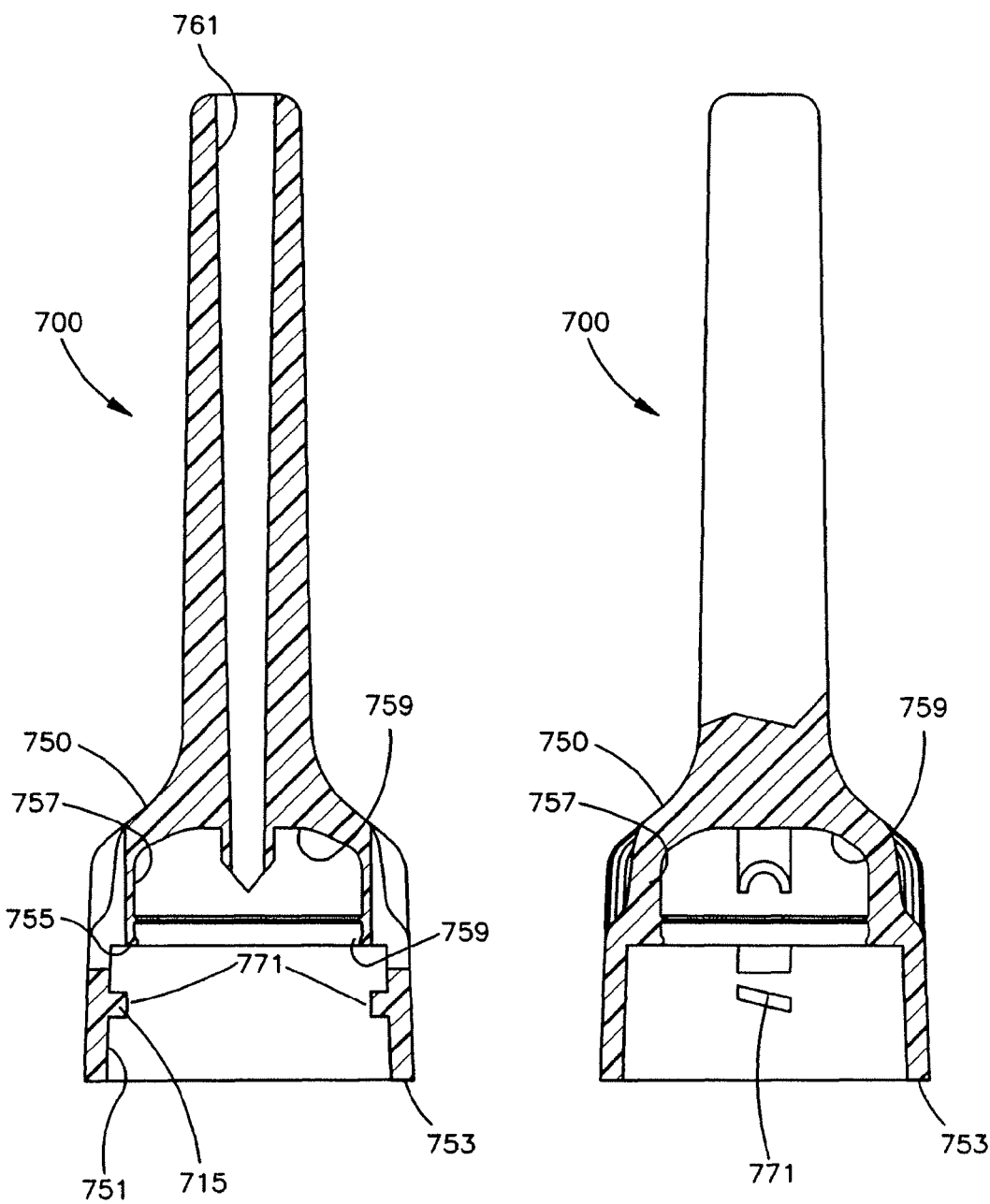
FIG. 7A is a cross-sectional view of a dispensing cap component of a fluid delivery assembly in accordance with an embodiment of the invention.
FIGS. 7B, 7C, and 7D are cut-away, perspective and top plan views, respectively, of the cap component of FIG. 7A.
Figure 7C:
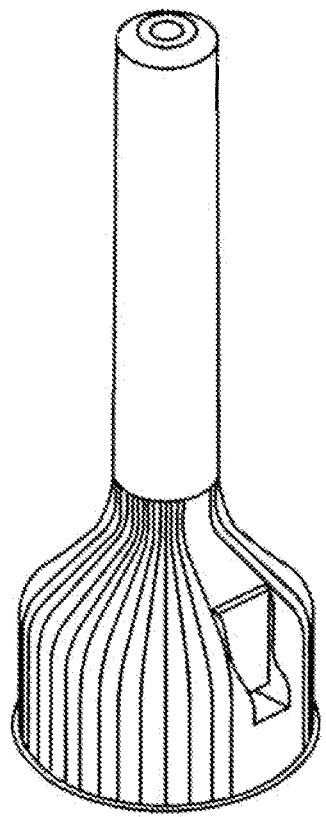
Figure 7D:
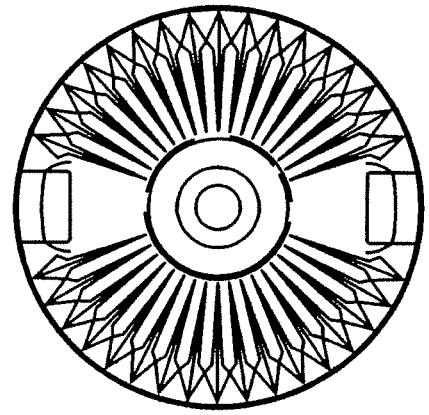
Figure 8:
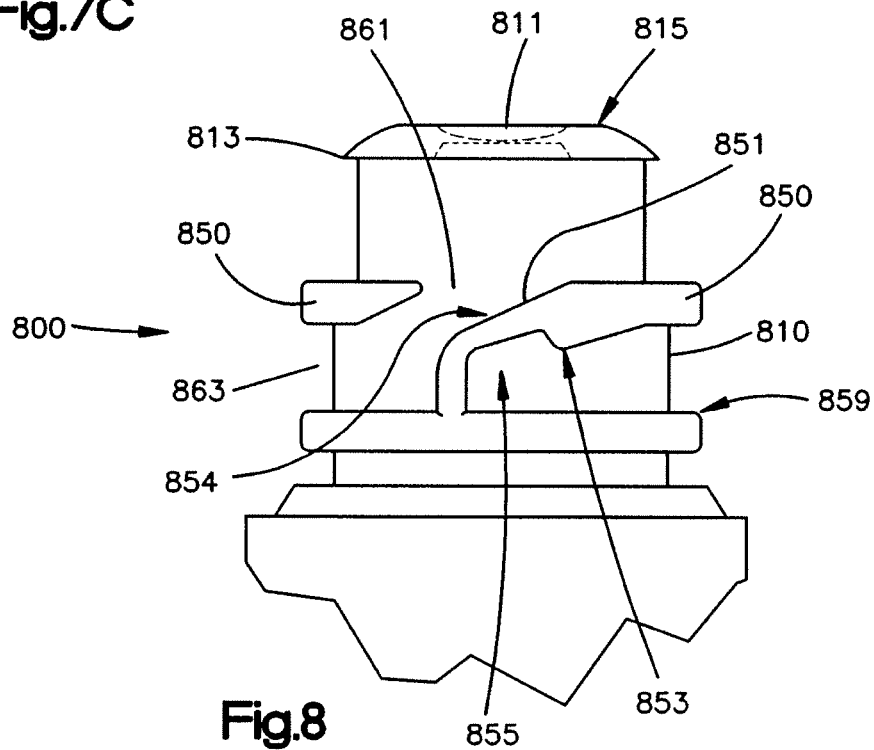
FIG. 8 is a perspective view of a fluid reservoir component of a fluid delivery assembly in accordance with an embodiment of the invention.

Another preferred embodiment of the invention is shown in FIG. 7 and FIG. 8. A dispensing cap 700, in accordance with another embodiment of the invention is shown generally in FIG. 7. Cap 700 is configured to work with a fluid or gel reservoir 800 shown generally in FIG. 8. The engagement between cap 700 and fluid reservoir 800 is accomplished via the use of a raised structure 850 and a pre-activation ridge 801 of a head region 810 of fluid reservoir 800 and a locking groove 773 and a pair of slanted cam followers 771 about an internal surface 751 of dome 750 thereof. They are shown as, but are not limited to being 180° apart and unitary with dispensing cap 700.

As shown in FIG. 7, internal wall 751 of dome 750 of dispensing cap 700 extends perpendicularly from edge 753 of dome 750 to approximately halfway up dome 750 where a smaller inside diameter of dome defines a second edge 755 and an internal wall 757. The lower junction of internal wall 757 is shaped into locking groove 773. Two regions of internal wall 751 of dome 750 of dispensing cap 700 are raised to form slanted cam followers 771. Slanted cam followers 771 are preferably positioned in the region between edges 753 of dome 750 to edge 755.

As shown in FIG. 8, the top surface 815 of head region 810 includes a pierceable region 811. A pair of pre-activation rims 850 on fluid reservoir 800 extend from and are unitary with fluid reservoir 800. One end of each pre-activation rim 850 adopts a downward slanting region 851, which further turns vertically downward to join a cap stabilizing ring 859. A pair of lug locks 855 are notches provided on the lower edges 853 of each of slanting region 851.

In an inactive configuration, a ridge 813 on head region 810 is engaged with a locking groove 759 to prevent accidental activation and dispensing cap 700 is captively held on head 810 of fluid reservoir 800 during transport or storage without piercing the pierceable region 819.

To put a channel 761 of cap 700 in communication with fluid reservoir 800, fluid reservoir 800 and dispensing cap 700 are pushed towards each other with sufficient force to urge ridge 813 on head region 810 out of locking groove 759 and rotated until slanted cam followers 771 advance through a pair of gaps 861 between and defined by pre-activation rims 850. Once cam followers 771 drop into gaps 861 and make contact with the upper edge of downward slanting region 854, dispensing cap 700 and fluid reservoir 800 may be turned so that slanted cam followers 771 move in spaces 863 between and defined by lower edge of pre-activation rims 850 and the upper edge of cap stabilizing ring 859 until cam followers 771 enter lug locks 855. During rotation, a piercing tip 740 is gradually lowered to penetrate pierceable region 813. In the activated condition, a top surface 815 of head region 810 contacts an inner ceiling 759 of dome 750, thereby creating a seal to prevent fluid leakage during dispensing.

Figure 9B:
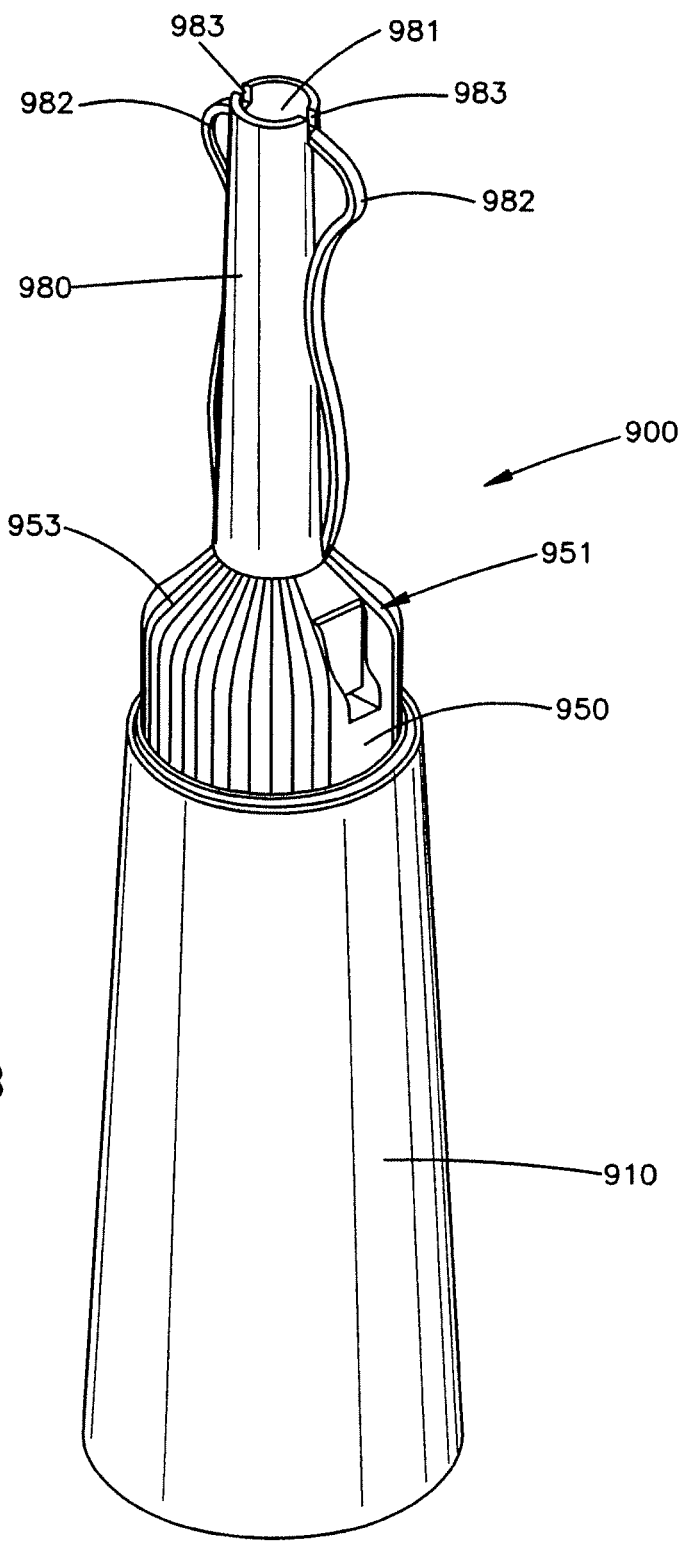

In another embodiment of the invention, shown in FIGS. 9A, 9B and 9C, dispensing cap 900 has a base 950 and an applicator tube 980. Dispensing cap 900 is configured to work with and dispense fluid from a fluid reservoir 910. A top surface 951 of base 950 contains a plurality of ridges 953 capable of providing the user a firm grip during activation. Applicator tube 980 contains two opposing fin structures 982 constructed and arranged to be able to part the fur coat of the animal. A nozzle end 981 of applicator tube 980 has a notch 983. When nozzle end 981 is in contact with the skin of the animal, the space formed between notch 983 and the skin permits the outflow of parasiticde. Fin structures 982 help part the animal's fur and the notch permits smooth fluid flow even if the tip is resting on the skin of the animal. It should be appreciated that the fur and insecticide spreading fins and the notch may adopt a wide variety of shapes and configurations.

Figure 10:
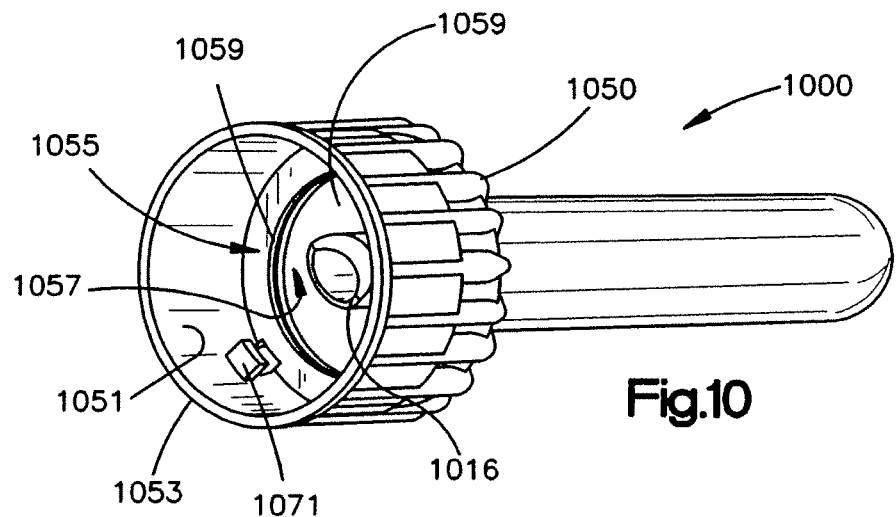
FIG. 10 is a perspective view of a dispensing cap component of a fluid delivery assembly in accordance with an embodiment of the invention.
Figure 11:
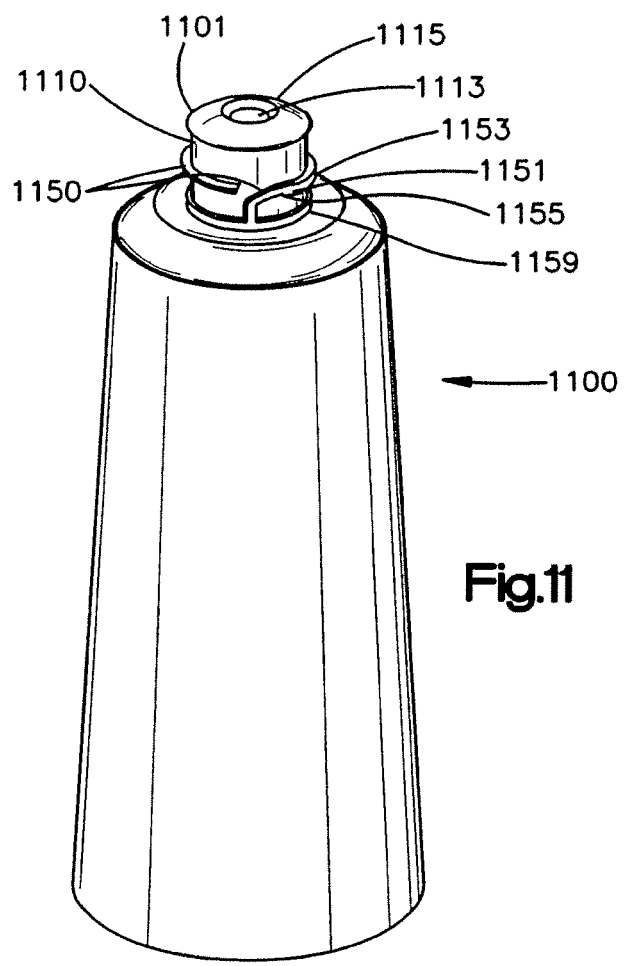
FIG. 11 is a perspective view of a fluid reservoir component of a fluid delivery assembly in accordance with an embodiment of the invention.

Another preferred embodiment of the invention is shown in FIG. 10 and FIG. 11. A dispensing cap 1000 shown generally in FIG. 10 is configured to work with a fluid reservoir 1100 shown generally in FIG. 11. It should be noted that the fluid reservoirs identified herein can also be gel reservoirs. The engagement between cap 1000 and fluid reservoir 1100 is accomplished via the use of a raised structure 1150 and a pre-activation ridge 1101 of a head region 1115 of fluid reservoir 1100 and a locking groove 1073 and a pair of slanted cam followers 1071 about an internal wall 1051 of dome 1050 thereof. These are shown as, but are not limited to, being 180° apart and unitary with dispensing cap 1000.

As shown in FIG. 10, internal wall 1051 of dome 1050 of dispensing cap 1000 extends perpendicularly from an edge 1053 of dome 1050 to approximately halfway up dome 1050 where a smaller inside diameter of dome defines an internal ledge 1055 and an internal wall 1057. The lower junction of internal wall 1057 is shaped into locking groove 1073. Two regions of internal wall 1051 of dome 1050 of dispensing cap 1000 are raised to form slanted cam followers 1071. Slanted cam followers 1071 are generally positioned in the region between edge 1053 of dome 1050 and edge 1055.

As shown in FIG. 11, a top surface of head 1115 includes a pierceable region 1113. A pair of pre-activation rims 1150 on fluid reservoir 1100 extend from and are unitary with fluid reservoir 1100. One end of each pre-activation rim 1150 adopts a downward slanting region 1151, which further turns vertically downward to join a cap stabilizing ring 1159. A pair of notched lug locks 1155 are provided on lower edges 1153 of each of slanting region 1151.

Figure 12A:
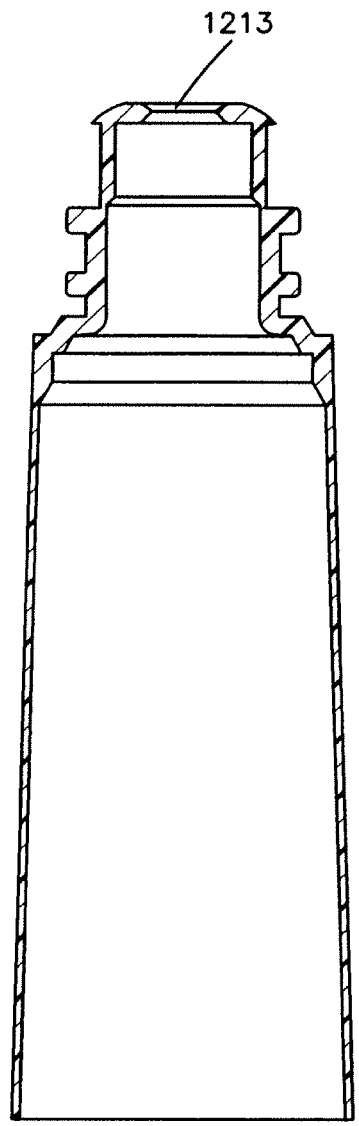
FIGS. 12A and 12B are a cross-sectional view and a side view of a fluid reservoir component of a fluid delivery assembly in accordance with an embodiment of the invention.
Figure 12B:
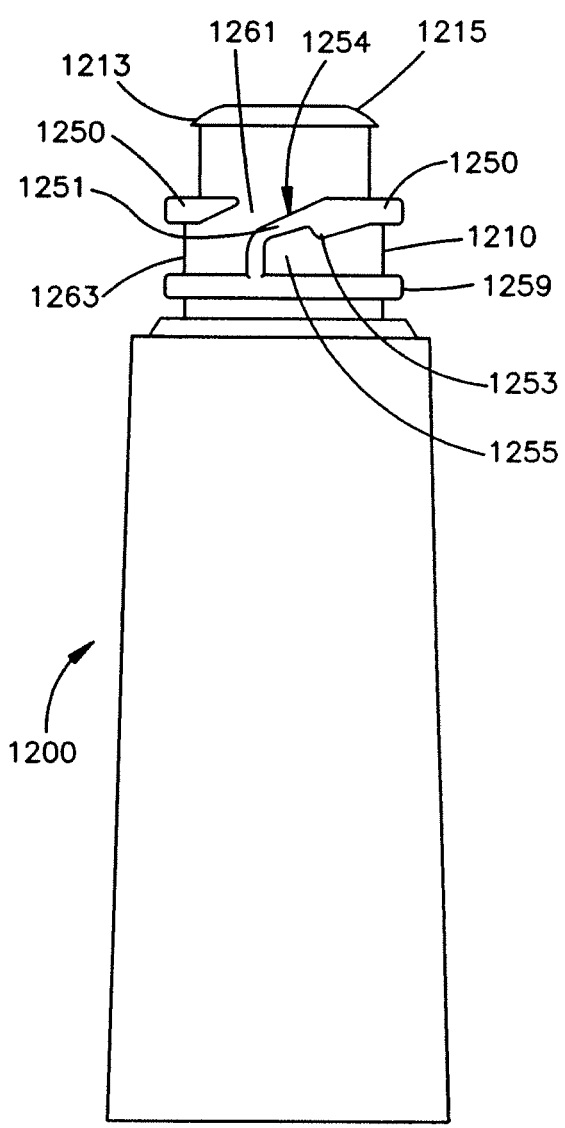

A fluid reservoir 1200 of another preferred embodiment of the invention are shown generally in FIGS. 12A and 12B. A top surface 1215 of a head 1210 includes a pierceable region 1213. A pair of pre-activation rims 1250 on fluid reservoir 1200 extend from and are unitary with fluid reservoir 1200. One end of each pre-activation rim 1250 adopts a downward slanting region 1251, which further turns vertically downward to join a cap stabilizing ring 1259. A pair of notched lug locks 1255 are provided on a lower edge 1253 of each of slanting region 1251.

Figure 13:
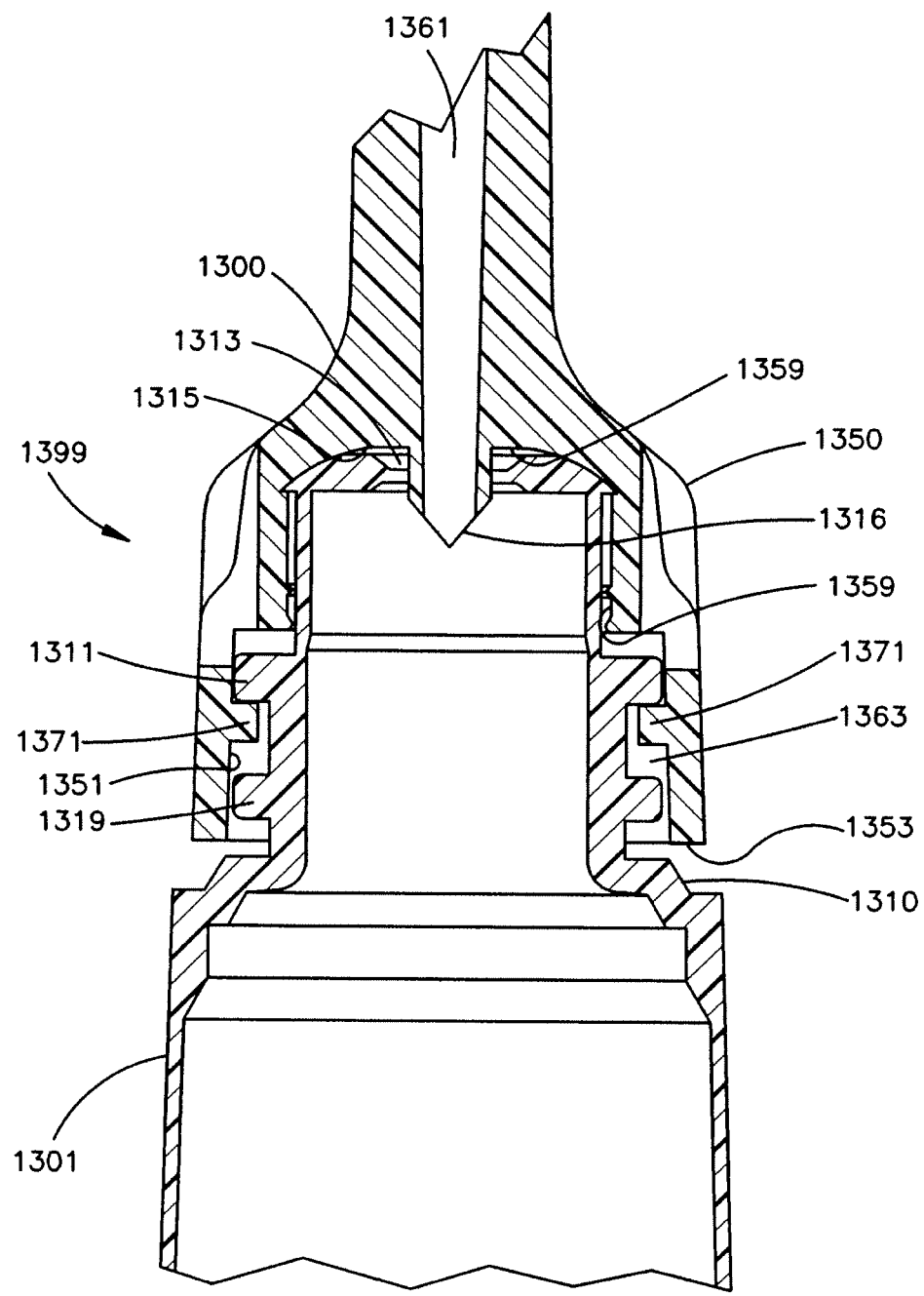
FIG. 13 is a partial cross-sectional view of a fluid delivery assembly in accordance with another embodiment of the invention in the post-activation condition.

The partial cross-sectional view of an activated configuration of a system in 1399 in accordance with still another embodiment of the invention is shown in FIG. 13. In the activated condition, a fluid channel 1361 of a cap 1300 pierces a pierceable region 1313 on a top surface 1315 of a head region 1310 of a fluid supply 1301 and is in fluid communication with fluid supply 1301. Top surface 1315 of head region 1310 contacts an inner ceiling 1359 of a dome 1350, thereby creating a seal to prevent fluid leakage during dispensing. A pair of cam followers 1371 on an inside wall 1351 of dome 1350 of cap 1300 travels in spaces 1363 between and defined by lower edge of a pre-activation rims 1311 and the upper edge of a cap stabilizing ring 1319 on head region 1310.

In another embodiment of the invention, the applicator tip branches into a forked dispensing manifold having multiple, preferably 2 to 5, and most preferably 3, projections or tines. At least one projection has an opening at the distal end to dispense fluid from the fluid reservoir.

Figure 14B:
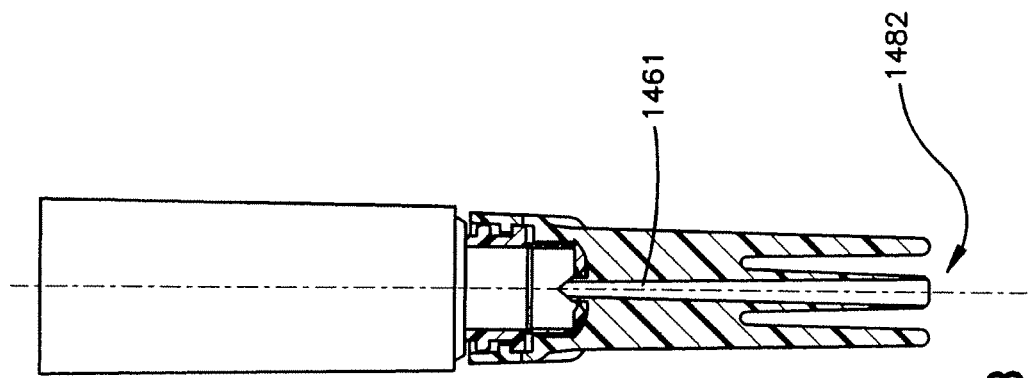
FIGS. 14A and 14B are perspective and cut-away views of a cap of a fluid delivery assembly in accordance with another embodiment of the invention.
Figure 14A:
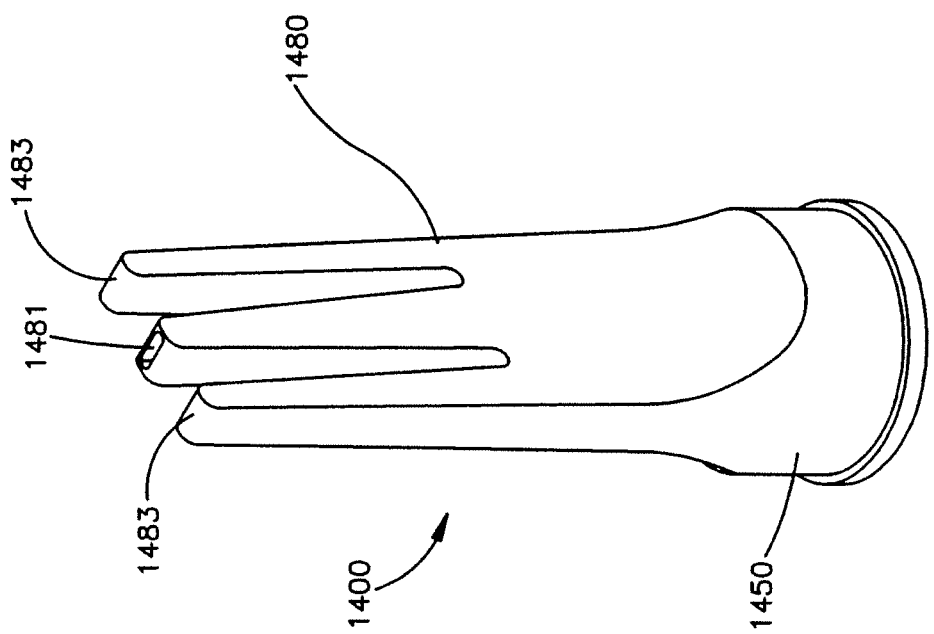

FIGS. 14A and 14B show an applicator cap 1400 of a fluid delivery assembly in accordance with another embodiment of the invention. The distal portion of cap 1400 is connected to a forked dispensing manifold 1480 having a central projection tine 1481 and two side projection tines 1483. The distal end of central tine 1481 has an opening 1482. A channel 1461 extends from opening 1482 along the length of central tine 1481 through a base 1450 of applicator cap 1400. Central tine 1481 and side tines 1483 can further adopt a elliptical or tapered circumference to aid the parting of hair. Other embodiments with four or more projections tines or dispensing ports at the end of each projection tines are acceptable.

Figure 15B:
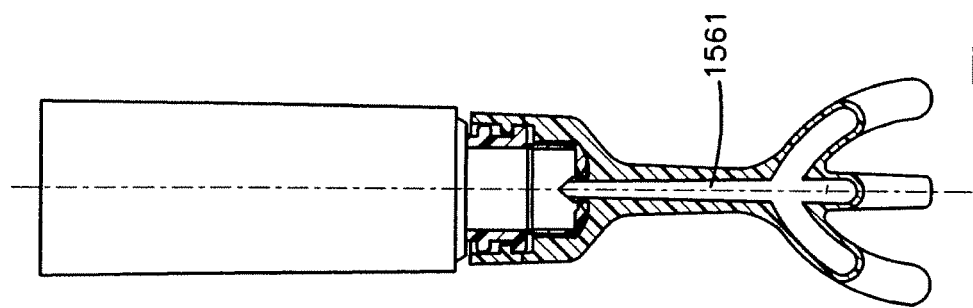
FIGS. 15A and 15B are perspective and cut-away views of a cap of a fluid delivery assembly in accordance with another embodiment of the invention.
Figure 15A:
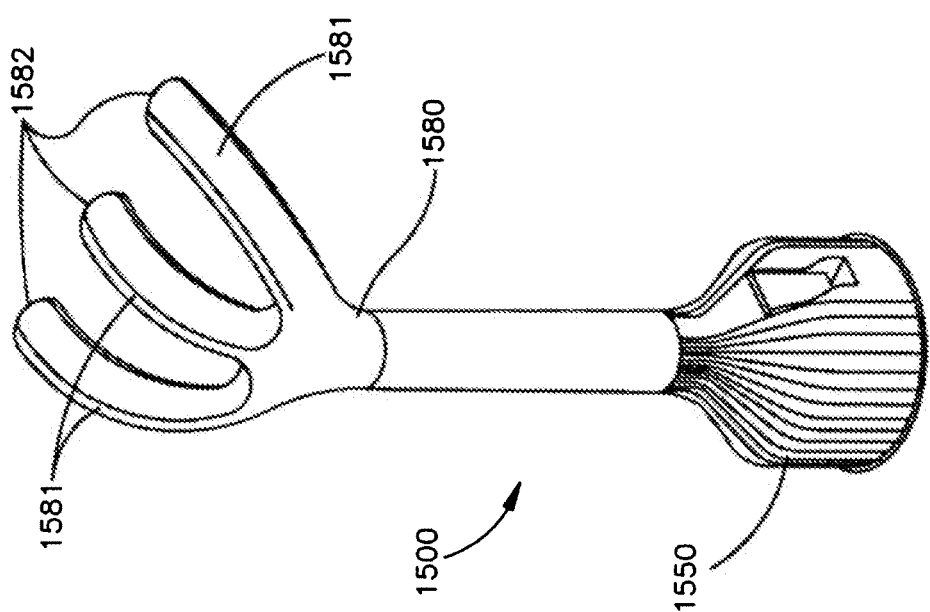

FIGS. 15A and 15B show an applicator cap 1500 of a fluid delivery assembly in accordance with another embodiment of the invention. The distal portion of cap 1500 is connected to a forked dispensing manifold 1580 having three projection tines 1581. The distal portion of tines 1581 are further curved from the plane of manifold 1580 to form a claw-like bend. The distal ends of one or more of tines 1581 each have an opening 1582. A branched channel 1561 extends from opening 1582 along the length of tines 1581 and dispensing manifold 1580 through a base 1550 of applicator cap 1500. Tines 1581, manifold 1580 and base 1550 may be constructed as an unitary piece or as separate pieces to be attached by the user over the end of a shorter tip.

FIGS. 16A and 16B show an applicator cap 1600 of a fluid delivery assembly in accordance with the invention. The distal portion of cap 1600 is connected to a forked dispensing manifold 1680 having three projection tines 1681. The distal portion of tines 1681 are tapered. The distal ends of tines 1691 each have an opening 1682. A branched channel 1661 extends from opening 1682 along the length of tines 1681 and dispensing manifold 1680 through a base 1650 of applicator cap 1600. Tines 1681, manifold 1680 and base 1650 may be constructed as an unitary piece or as separate pieces to be attached by the user over a shorter tip structure.

The examples provided herein are merely exemplary, as a matter of application specific to design choice, and should not be construed to limit the scope of the invention in any way.

In one embodiment of the invention the tube for delivering the liquid or gel is about 15 to 25 mm long, preferably 18 to 20 mm long and has an internal diameter of about 1 to 4 mm, preferably 2 to 3 mm.

In an embodiment of the invention, the reservoir has a volume of about 0.01 to 100 ml.

Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall therebetween.

What is claimed is:

1. A fluid dispensing system, comprising:
 a reservoir portion having a cap mounting neck and containing a fluid, the reservoir having a pierceable opening at the distal end of the neck;
 a cap including a piercing tip and an elongated applicator tube portion having an opening at its distal end, with the lumen of the tube in fluid communication with the piercing tip, mounted on the neck of the reservoir;
 the cap and neck constructed and arranged to adopt at least one active configuration with the piercing tip extending through the pierceable opening to place the reservoir in fluid communication with the lumen of the applicator tube and at least one inactive configuration with the piercing tip distal to the pierceable opening of the reservoir;
 the cap including at least two inwardly projecting tabs;
 the neck of the reservoir portion including at least two outwardly extending horizontal ridges that extend only part of the way around the neck, with at least two ramp portions, extending proximally from the horizontal ridges at an angle to the ridges, and defining a passageway from the distal side of the horizontal ridges to the proximal side of the horizontal ridges, the horizontal ridge and ramp portions configured to interact with the tabs to selectively maintain said piercing tip in a position away from the pierceable opening in the inactive configuration and to advance the piercing tip into the active configuration by the selective application of twisting force to bring the tabs through the passageway and the piercing tip in the proximal direction towards the pierceable opening; and
 a projecting fin structure at the distal opening of the tube extending proximally along at least a portion of the length of the outside surface of the elongated tube, the fin structure configured and positioned to help part an animal's fur and direct fluid from the tube, past an animal's fur, onto the skin of an animal.

2. The fluid dispensing system of claim 1, wherein the inwardly projecting tabs comprise camming surfaces which interact with ridges on the neck so that directed twisting of the cap with respect to the reservoir will urge the cap from the inactive to the active configuration.

3. The fluid dispensing system of claim 1, wherein the neck comprises at least two horizontal ridges that each extend only part of the way around the neck, perpendicular to an axis of the tube and at least two ramp portions extending proximally from the horizontal ridge at a non-perpendicular angle to the axis, the horizontal ridge portions and ramp ridge portions on the outside of the neck, facing the cap and the ramp ridge portion defining a passageway from the distal side of the horizontal ridge portion to the proximal side of the horizontal ridge portion.

4. The fluid dispensing system of claim 1, wherein the reservoir stores a single dose of at least one parasiticide for animals.

5. The fluid dispensing system of claim 1, wherein the cap comprises forked projections and the forked projections extend substantially straight out from the cap.

6. The fluid dispensing system of claim 1, wherein the fin extends substantially along the entire outside length of the tube.

7. The fluid dispensing system of claim 1, wherein at least one notch is present on the cap and at least one fluid dispensing port is associated with the notch, the notch and the at least one fluid dispensing port are constructed and arranged to permit the outflow of fluid from the fluid dispensing port when the distal end of the cap is resting on the skin of the animal.

8. A fluid dispenser, comprising:
 a reservoir having a neck and a cap coupled to the neck, the neck having a pierceable opening at its distal end;
 a cap including a piercing tip and an elongated applicator tube portion having an opening at its distal end, with the lumen of the tube in fluid communication with the piercing tip;
 the cap and neck constructed and a anged to adopt at least one active configuration with the piercing tip extending through the pierceable opening to place the reservoir in fluid communication with the lumen of the applicator tube and at least one inactive configuration with the piercing tip distal to the pierceable opening of the neck;
 the cap including at least two inwardly projecting tabs; and
 the neck including at least two outwardly extending horizontal ridges that extend only part of the way around the neck, with at least two ramp portions, extending proximally from the horizontal ridges at an angle to the ridges, and defining a passageway from the distal side of the horizontal ridges to the proximal side of the horizontal ridges, the horizontal ridge and ramp portions configured to interact with the tabs to selectively maintain said piercing tip in a position away from the pierceable opening in the inactive configuration and to advance the piercing tip into the active configuration by the selective application of twisting force to bring the tabs through the passageway and the piercing tip in the proximal direction towards the pierceable opening.

9. The fluid dispenser of claim 8, wherein the tube includes an outwardly projecting fin and the fin is widest at its distal end and tapers to the outside wall of the tube.

10. The fluid dispenser of claim 8, wherein at least one notch is present at the opening at the distal end of the dispensing tube, the notch and the opening are constructed and arranged to permit the outflow of fluid from the fluid dispensing port when the distal end of the tube is resting on the skin of the animal.

11. The fluid dispenser of claim 8, wherein the tube includes an outwardly projecting fin and the outer edge of the fin is curved.

12. The fluid dispenser of claim 8, wherein the tube includes an outwardly projecting fin and the fin extends substantially straight in a radial direction from the tube.

13. The fluid dispenser of claim 8, wherein the reservoir stores at least one parasiticide.

* * * * *